United States Patent
Pittaway et al.

(10) Patent No.: US 7,383,852 B2
(45) Date of Patent: Jun. 10, 2008

(54) SELF SEALING WATER TRAP

(75) Inventors: Alan Pittaway, Bucks (GB);
Surinderjit Kumar Jassell, Middlesex (GB); Simon Robert Payne, Surrey (GB)

(73) Assignee: Intersurgical AG, Vaduz (LI)

(*) Notice: Subject to any disclaimer, the term of this patent is extended or adjusted under 35 U.S.C. 154(b) by 107 days.

(21) Appl. No.: 10/497,956

(22) PCT Filed: Dec. 6, 2002

(86) PCT No.: PCT/GB02/05533

§ 371 (c)(1),
(2), (4) Date: Jan. 25, 2005

(87) PCT Pub. No.: WO03/047674

PCT Pub. Date: Jun. 12, 2003

(65) Prior Publication Data

US 2005/0121074 A1 Jun. 9, 2005

(30) Foreign Application Priority Data

Dec. 7, 2001 (GB) .................. 0129296.0

(51) Int. Cl.
*F16T 1/34* (2006.01)
(52) U.S. Cl. ............... 137/171; 137/454.6; 55/429; 55/433; 251/149.9
(58) Field of Classification Search ............. 137/171, 137/203, 454.6; 55/429, 433; 251/149.9
See application file for complete search history.

(56) References Cited

U.S. PATENT DOCUMENTS

| | | | | |
|---|---|---|---|---|
| 1,467,511 A | * | 9/1923 | Smith et al. ............ | 137/203 |
| 2,778,448 A | * | 1/1957 | Graves .................. | 137/171 |
| 3,214,054 A | * | 10/1965 | Poethig et al. .......... | 220/240 |
| 4,417,574 A | | 11/1983 | Talonn et al. | |
| 4,457,305 A | | 7/1984 | Shanks et al. | |
| 5,168,868 A | * | 12/1992 | Hicks .................. | 128/205.12 |

FOREIGN PATENT DOCUMENTS

| | | |
|---|---|---|
| EP | 0 460 731 A1 | 12/1991 |
| EP | 0 705 616 A1 | 4/1996 |
| GB | 1 456 570 A | 11/1976 |
| GB | 2 272 745 A1 | 5/1994 |
| WO | WO 01 78819 A1 | 10/2001 |

\* cited by examiner

*Primary Examiner*—John Rivell
*Assistant Examiner*—Craig M Schneider
(74) *Attorney, Agent, or Firm*—Nixon Peabody LLP

(57) ABSTRACT

A water trap suitable for use in a mechanical ventilation circuit comprising a cap with an inlet and an outlet, a fluid collection vessel engageable with the cap, and a rotatable closure with at least one aperture interposed between the cap and the vessel. The vessel is operably linked to the closure such that engagement or disengagement of the vessel from the cap causes the closure to be rotated. The cap is formed with an internal partition extending into abutment with the closure to define a chamber via which the inlet and outlet are in fluid communication and the closure forming a base of the chamber. When the vessel is engaged with the cap, the closure has a first orientation in which the at least one aperture is located within the periphery of the skirt in the base of the chamber and the vessel is in communication with the chamber via the at least one aperture. When the vessel is removed from the cap the closure is rotated to a second orientation in which the at least one aperture is located externally of the periphery of the skirt and the base of the chamber.

33 Claims, 4 Drawing Sheets

SELF SEALING WATER TRAP

This application is a national stage application under 35 U.S.C. § 371 from PCT Application No. PCT/GB02/05533 filed Dec. 6, 2002, which claims the priority benefit of Great Britain Application No. 0129296.0 filed Dec. 7, 2001.

FIELD OF THE INVENTION

This invention relates to a self-sealing water trap, and in particular to such a trap which is of utility in systems for the mechanical ventilation of a patient incapable of spontaneous respiration.

BACKGROUND in a healthy person the function of breathing is entirely spontaneous. The brain senses a build-up of carbon dioxide in the blood and immediately calls for more oxygen. This oxygen is taken into the body by spontaneous inspiration and carbon dioxide is removed in the passive exhalation phase of respiration. A healthy person generates a certain amount of humidity, which is used in the lung to stop the build-up of secretions.

The ability to breathe spontaneously may be lost for a number of reasons. Examples are as a result of surgical procedures (post-operatively), as a result of certain muscular disorders affecting the lung, or as a result of sedation by a clinician. Patients thus affected must be ventilated by mechanical means in order to achieve oxygenation and carbon dioxide removal.

When a patient is mechanically ventilated it is essential that the humidity of the air is maintained at a sufficiently high level, since a lung with impaired function will be more susceptible to secretions. This can be achieved using a heat-moisture exchanger (HME) or a heated water bath humidifier. An HME retains the moisture in an exhaled breath and this moisture is sent back to the lung with the next inspiratory phase. In a water bath system the inspiratory gas is passed through a heated water chamber and picks up humidity prior to entering the lung. As the humid inspiratory gas travels along the breathing system a certain amount of water vapour will cool and start to condense, forming water droplets, which will start to build up, causing so-called "rain-out".

Such water has to be removed from the breathing system so that it does not occlude the respiratory air flow or drain back into the patient's lungs thereby putting the patient at risk of drowning, or does not drain into the ventilator/anaesthetic equipment thus causing damage. If it is allowed to accumulate for a protracted period then due to its non-compressible nature the water will effectively block the breathing system.

The most effective way of collecting moisture in such a system is by the use of a device called a water trap. Such a device is generally located at the mid-point of the breathing system and positioned at the lowest point so that liquid will drain into it. It is necessary periodically to empty accumulated water from such a water trap and this should ideally be possible without interrupting ventilation of the patient and also without causing a drop in the pressure within the system, and without permitting escape of possibly contaminated or infectious fluid from the system or infection of the system by external agents.

EP 0705616 discloses one solution to this problem which utilises a two disc valve arrangement with each disc including a semi-circular aperture. The valve is opened and closed by the apertures being brought into or out of registration respectively. WO 01/78819 discloses another solution which also utilises a two disc valve arrangement. This arrangement however uses two apertures in each disc surrounded by elastomeric seals to improve the sealing ability of the valve. The construction of these water traps is relatively complicated with each water trap comprising several separate components.

SUMMARY

There has now been devised an improved form of water trap.

According to the invention there is provided a water trap suitable for use in a mechanical ventilation circuit, the water trap comprising a cap having formed therein an inlet and an outlet, a fluid collection vessel engageable with the cap, and a rotatable closure interposed between the cap and the fluid collection vessel and including at least one aperture, the arrangement being such that the fluid collection vessel is operably linked to the closure such that engagement or disengagement of the fluid collection vessel from the cap causes the closure to be rotated, wherein the cap is formed with an internal partition extending into abutment with the closure so as to define a chamber via which the inlet and outlet are in fluid communication, such that when the fluid collection vessel is engaged with the cap the closure has a first orientation in which the fluid collection vessel is in communication with the chamber via the at least one aperture in the closure, and when the fluid collection vessel is removed from the cap the closure is rotated to a second orientation in which the at least one aperture is located externally of the chamber.

The water trap according to the invention is advantageous primarily in that the removal of the collection vessel from the trap, eg for emptying, automatically rotates the closure, and re-engagement of the collection vessel subsequently automatically restores communication between the chamber and the collection vessel. This eliminates or substantially mitigates disadvantages associated with the prior art, such as interruption of ventilation, a reduction in internal pressure in the system, leakage of fluid from the system or contamination of the system from outside. Furthermore, the construction of the water trap according to the invention is much simpler than the construction of the prior art.

The partition conveniently takes the form of a skirt which depends from the underside of the cap, and surrounds the openings of the inlet and outlet. The skirt is preferably elongate in shape, being generally oblong in cross-section, ie having a length that is greater than (more commonly at least twice as great as) its width. The ends of the skirt are preferably rounded. The skirt thus preferably has a pair of parallel sides joined by rounded end portions.

The skirt may be integrally formed within the cap or may be formed separately from the cap. Where the skirt is a separate component, the cap preferably includes formations which engage the skirt. Such formations conveniently take the form of a rib onto which the skirt is pressed with an interference fit.

Preferably, a resilient seal is provided between the lower edge of the partition and the surface of the closure. The seal may be affixed to the closure, but is more preferably attached to the lower edge of the partition.

The seal is preferably formed in elastomeric material and the remainder of the cap and/or skirt is preferably formed in relatively rigid plastics material. These materials may be any such materials which are suitable for use in medical respiratory apparatus and together provide an effective seal. The component that carries the seal (most preferably the cap and/or skirt) is preferably formed using a two-shot injection moulding process which involves injection moulding the relatively rigid plastics material and subsequently injection moulding the elastomeric material that forms the seal onto the relatively rigid plastics material.

The rotatable closure preferably has the form of a disc, and may be received within the cap with a snap fit.

The collection vessel is operably linked to the rotatable closure such that the closure is rotated by rotation of the collection vessel, such rotation also releasing the collection vessel from the rest of the trap. The collection vessel most preferably has a quick release type connection to the rest of the trap, eg a bayonet-type fitting or similar.

According to another aspect of the invention there is provided a mechanical ventilation circuit including a water trap as described above.

BRIEF DESCRIPTION OF THE DRAWINGS

The invention will now be described in greater detail, by way of illustration only, with reference to the accompanying drawings, in which.

DETAILED DESCRIPTION

Figure 1:
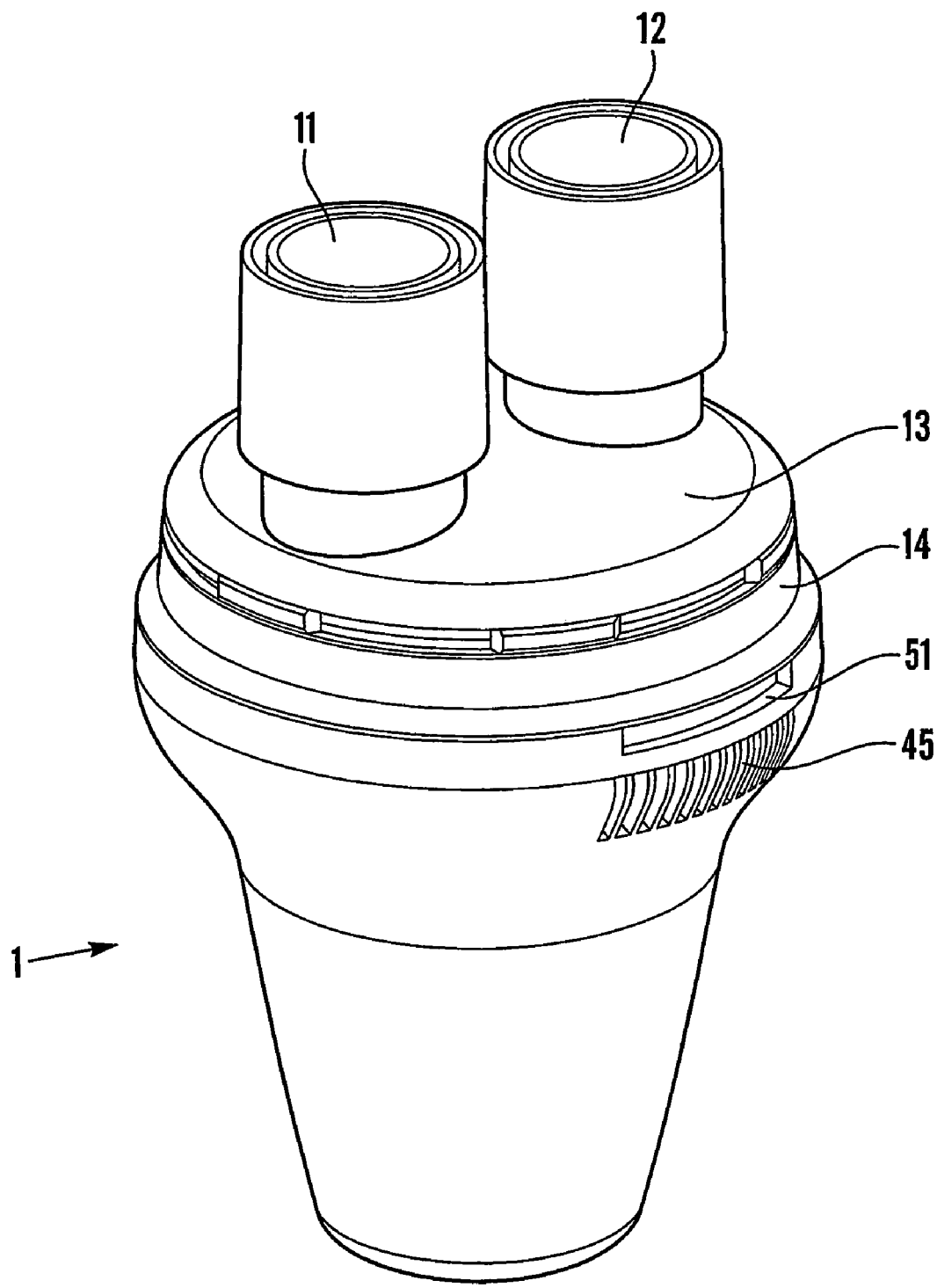
FIG. 1 is a perspective view of a first embodiment of a self sealing water trap according to the invention.
Figure 3:
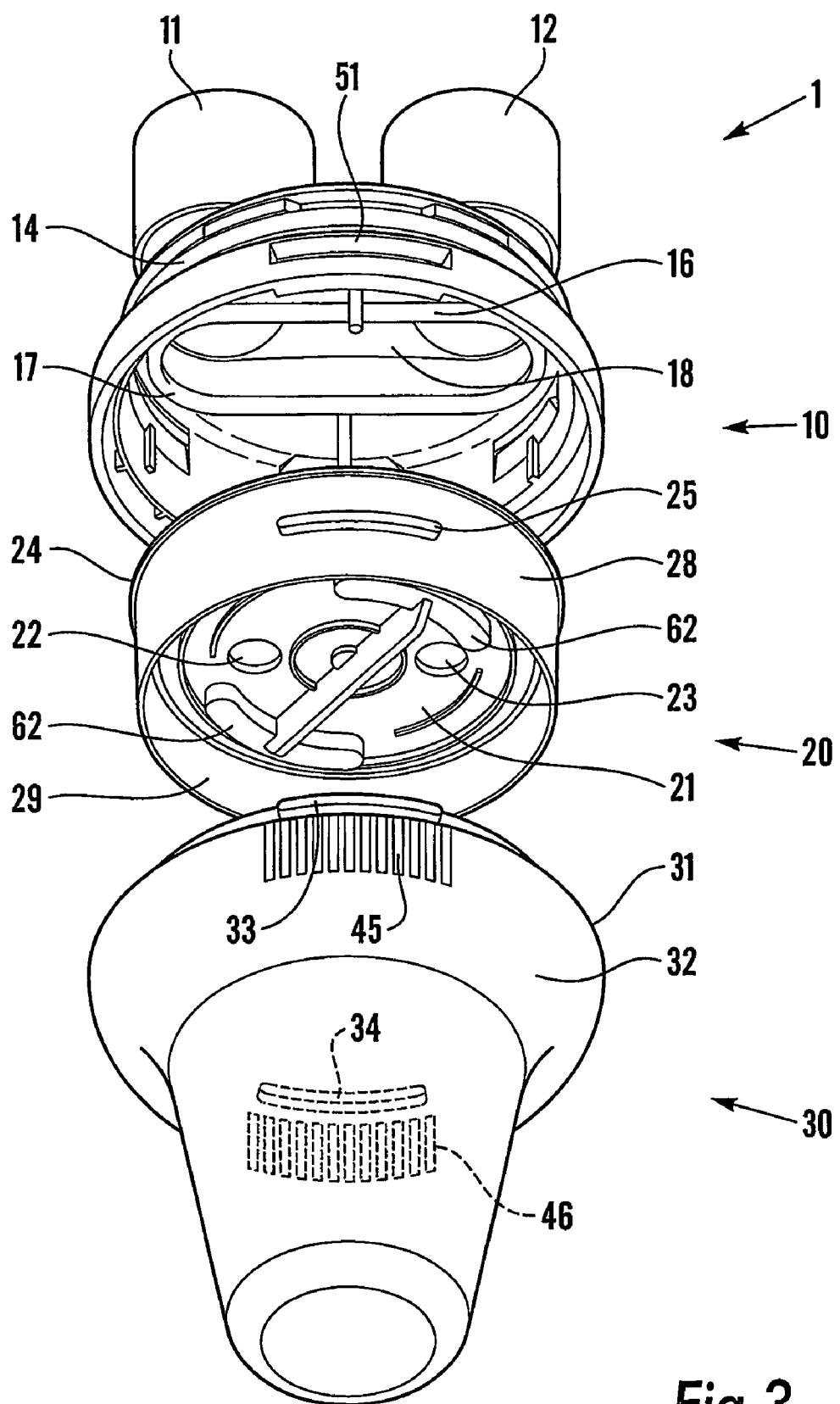
FIG. 3 is an exploded view of the water trap.

Referring first to FIG. 1, a self sealing water trap according to the invention is generally designated 1 and comprises essentially three components (see FIG. 3). These are a trap top 10, a valve plate 20 and a collecting cup 30. The three components 10,20,30 are each moulded in plastics material, the trap top 10 being formed in two different materials in a two-shot moulding process, as described below.

The trap top 10 is formed integrally with an inlet 11 and an outlet 12 which, in use, are connected to flexible conduits (not shown) forming part of a mechanical ventilation circuit. The trap top 10 has a generally flat central portion 13 (from which the inlet 11 and outlet 12 extend) and a downwardly depending peripheral skirt 14.

Figure 2:
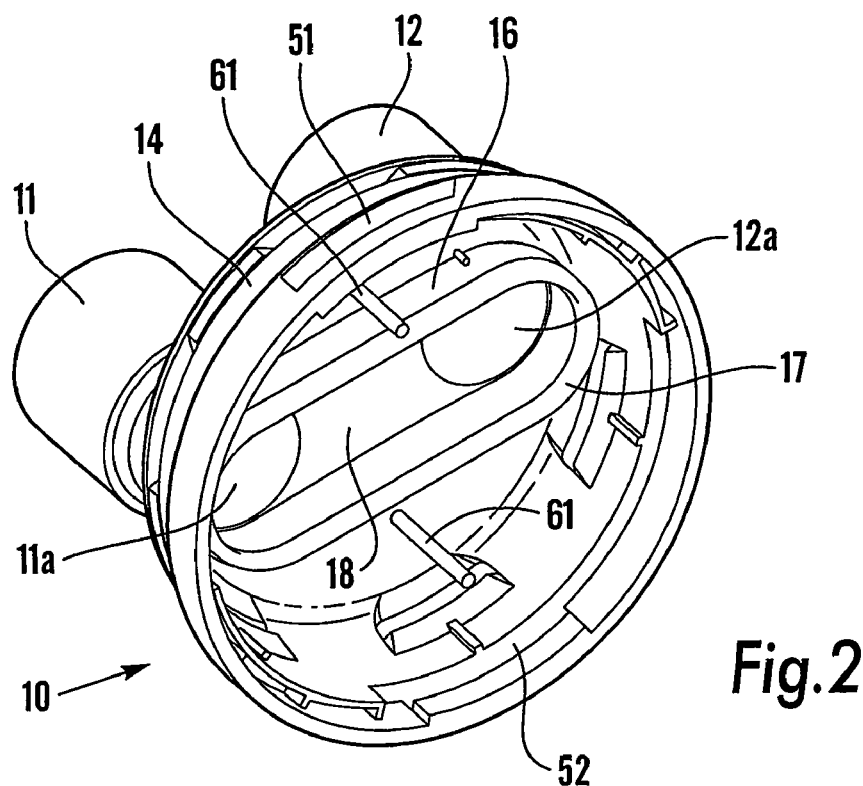
FIG. 2 is an internal perspective view of the trap top of the first embodiment of the self sealing water trap according to the invention.

Referring now to FIG. 2, an internal sealing skirt 16 depends downwardly from the underside of the central portion 13. The sealing skirt 16 surrounds both the inlet opening 11a and the outlet opening 12a located on the underside of the central portion 13 such that the sealing skirt 16 forms the wall of a chamber 18 which connects the inlet 11 and outlet 12 in fluid communication. The sealing skirt 16 includes an elastomeric seal 17 on its lower edge. The trap top 10 is made (apart from the seal 17) of a rigid plastics material to which the elastomeric material is applied, the trap top 10 including the seal 17 being formed in a two-shot moulding process. Such a process offers manufacturing advantages, but the substrate and the elastomeric components may alternatively be separately moulded components.

A pair of downwardly (with the trap 1 upright, as shown in FIGS. 1 and 3) projecting location pins 61 are formed integrally with the trap top 10 and cooperate with recesses 62 in the valve plate 20, as described below.

Referring now to FIG. 3, the valve plate 20 comprises a circular disc 21 with a pair of apertures 22,23. The apertures 22,23 are of smaller dimensions to the inlet and outlet openings 11a,12a. The apertures 22,23 are positioned in the disc 21 such that, with the valve plate 20 in a first orientation, the apertures 22,23 are in the base of the chamber 18 (ie within the periphery of the sealing skirt 16), and with the valve plate 20 in a second orientation, the apertures 22,23 are not in the base of the chamber 18 (ie outside the periphery of the sealing skirt 16).

The disc 21 has a peripheral annular flange with upwardly and downwardly extending limbs (28,29 respectively), the disc 21 thus being generally of H-section. The upwardly extending limb 28 has, at its uppermost extent, an outwardly projecting lip 24 which engages a corresponding shoulder on the internal surface of the skirt 14 of the trap top 10 with a snap fit. The valve plate 20 is thus captivated by the trap top 10, the disc 21 being held in abutment with the sealing skirt 16 of the trap top 10 and in particular with the elastomeric seal 17. The valve plate 20 is rotatable within the trap top 10. To ensure correct alignment of the assembly, the location pins 61 are received within arcuate recesses 62 formed in the disc 21.

A pair of part-circumferential lugs 25 (only one shown) extend outwardly from the valve plate 20, at diametrically opposed positions.

The collecting cup 30 is of upwardly increasing diameter, the upper part of the cup 30 being of double-walled construction. The outer wall 31 is flared to a diameter matching that of the skirt 14 of the trap top 10. The inner wall 32 projects upwards and is of sufficient diameter to fit between the skirt 14 and the downwardly extending limb 29 of the peripheral flange of the valve plate 20, the inner wall 32 fitting relatively closely about the limb 29.

The inner wall 32 is formed with a pair of diametrically opposed outwardly recessed parts which define recesses 33,34. These recesses 33,34 correspond in shape and dimensions to the lugs 25,26 on the valve plate 20. The recesses 33,34 are undercut such that the recesses 33,34 constitute bayonets which can be received within keeps 51,52 formed in the interior of the skirt 14 of the trap top 10. The external surface of the cup 30 immediately below the bayonets is ridged to form finger grips 45,46.

In the normal operating condition, the inlet 11 and outlet 12 of the water trap 1 are connected to respective conduits of a mechanical ventilation circuit. The trap 1 is located substantially at the mid-point of the circuit and at its lowest point. The cup 30 is engaged with the valve plate 20 and held in place by engagement of the bayonets in the keeps 51,52. In this condition, the apertures 22,23 and the sealing skirt 16 are aligned such that air entering the trap 1 via the inlet 11 can also enter the cup 30 before being drawn out through the outlet 12. Water in the system drains into the trap 1, and moisture carried by the air stream impacts upon the sides of the cup 30 and/or on other exposed internal surfaces of the trap 1, eg the top of the valve plate 20 and the interior of the sealing skirt 16, and drains into the cup 30 where it collects.

When it is desired to empty the cup 30, it is simply grasped by means of the finger grips 45,46 and twisted through 90°. This action releases the bayonets from the keeps 51,52 and enables the cup 30 to be removed from the assembly of trap top 10 and valve plate 20.

Because the recesses 33,34 receive the lugs 25,26 the valve plate 20 rotates with the cup 30. Thus, rotation of the cup 30 rotates the valve plate 20 in such a manner that the apertures 22,23 are located beyond the exterior of the sealing skirt 16 and therefore no longer form part of the chamber 18 wall. The chamber 18 is sealed by the upper surface of the disc 21 and the elastomeric seal 17 of the sealing skirt 16, preventing the passage of air through the apertures 22,23. Thus, removal of the cup 30 for emptying automatically seals the trap 1. The integrity of the breathing circuit is thereby maintained, ensuring that the circuit remains airtight during emptying of the cup 30, with no drop in pressure, leakage of fluid or risk of infection by external agents.

When the cup 30 is removed, air can still flow from the inlet 11 to the outlet 12 via the chamber 18.

The base of the bayonet has a downward projection (not shown) which constitutes an end-stop. The end-stop engages a corresponding formation on the internal surface of the skirt 14 when the cup 30 is rotated for release from the rest of the trap 1, thereby limiting rotation of the cup 30 and facilitating such release.

The lower surface of the keeps 51,52 and the mating faces of the bayonets are shaped to engage with a camming action. This facilitates secure engagement of the cup 30 with the rest of the trap 1, and inhibits unintentional release of the cup 30.

The trap top 10 and the valve plate 20 are most preferably moulded in plastics materials with low coefficients of friction to provide minimal resistance between the components when the water trap 1 is opened and closed.

Figure 5:
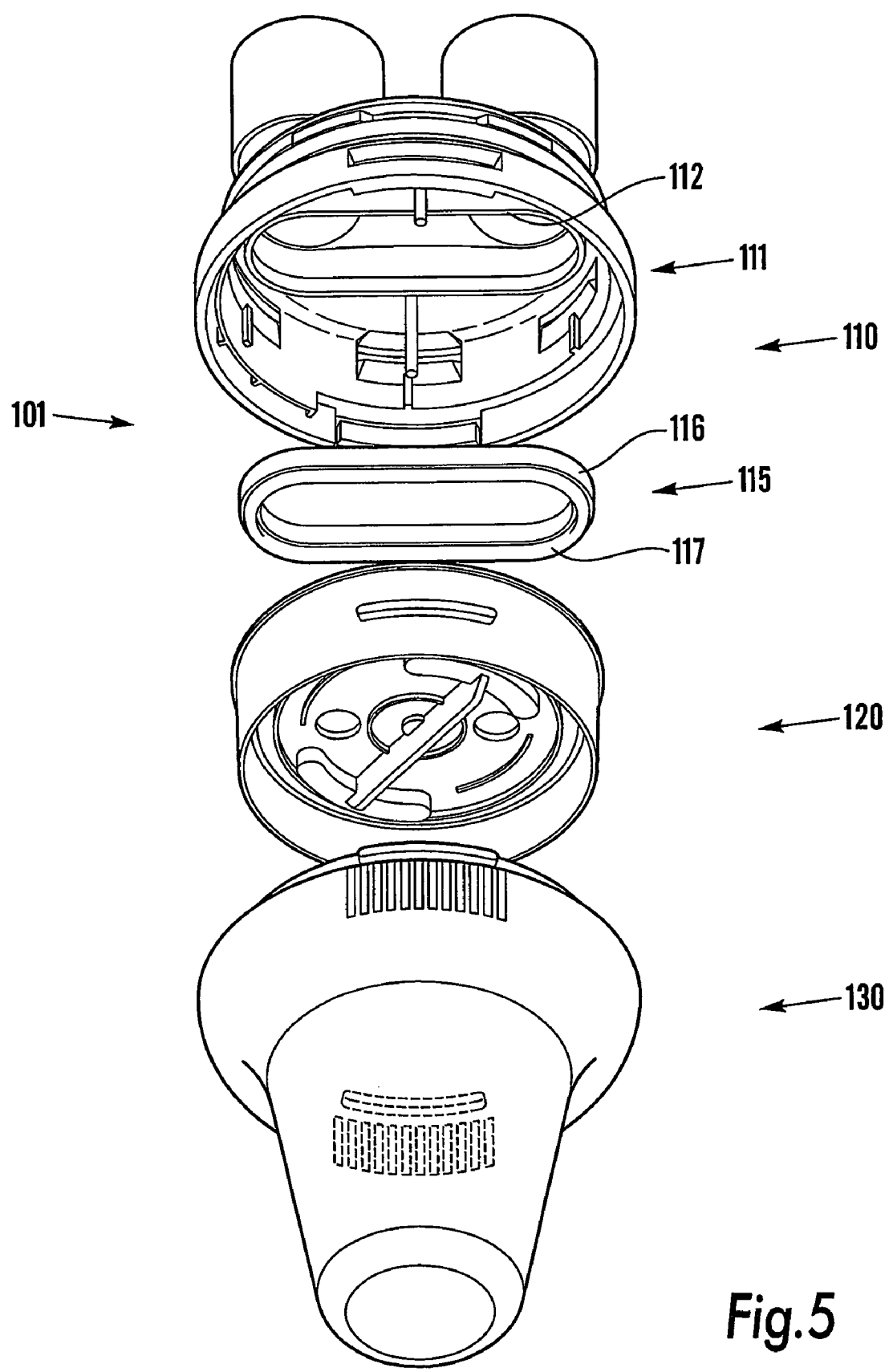
FIG. 5 is an exploded view of the second embodiment of the water trap.

Referring now to FIG. 5, a second embodiment of the self sealing water trap according to the invention is generally designated 101. The valve plate 120 and collecting cup 130 are identical to the valve plate 20 and the collecting cup 30 of the first embodiment 1. The external appearance of the second embodiment 101 is identical to that of the first embodiment 1, as shown if FIG. 1. The trap top 110, however, comprises two components as opposed to the single component trap top 10 of the first embodiment 1.

The first component 111 is identical to the trap top 10 of the first embodiment 1 save that the sealing skirt 16 of the first embodiment 1 has been replaced by a rib 112 of reduced height which carries no elastomeric seal. The first component 111 is therefore simply moulded in plastics material.

The second component 115 comprises a sealing skirt 116 of similar shape to the sealing skirt 16 of the first embodiment 1. The sealing skirt 116 is dimensioned to fit closely with an interference fit around the exterior of the rib 112. The lower edge of the sealing skirt 116 (as viewed in FIG. 5) includes an elastomeric seal 117. The second component 115 is therefore formed in two different materials in a two-shot moulding process.

Figure 4:
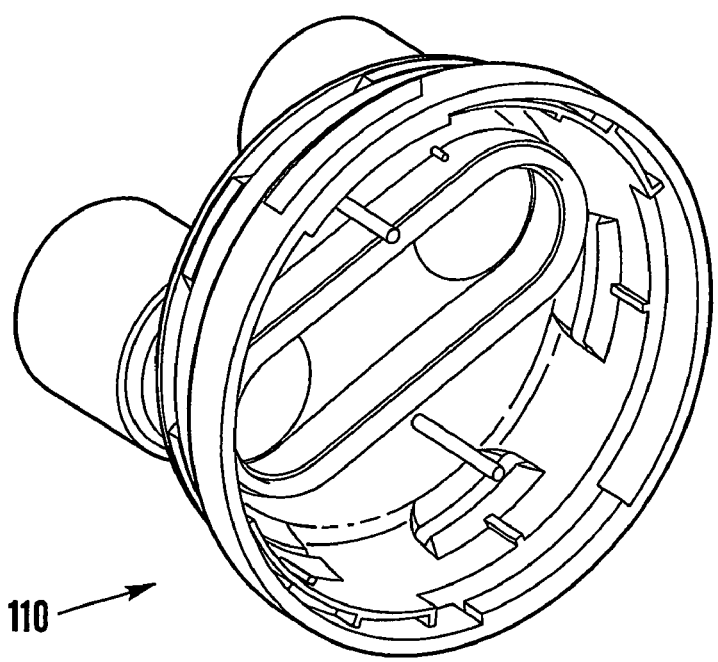
FIG. 4 is an internal perspective view of a sealing skirt engaged with a trap top which forms part of a second embodiment of the self sealing water trap according to the invention.

The first and second components 111,115 are engaged with an interference fit, as shown in FIG. 4. In use, the second embodiment 101 of the self sealing water trap is identical to the first embodiment 1.

The invention claimed is:

1. A mechanical ventilation system comprising:
 a cap having an inlet and an outlet;
 a fluid collection vessel engageable with the cap;
 a rotatable closure interposed between the cap and the fluid collection vessel and including at least one aperture, the fluid collection vessel is operably linked to the closure such that movement of the fluid collection vessel from the cap causes the closure to be rotated;
 wherein the cap is formed with an internal partition in the form of a skirt that extends into abutment with the closure to define a chamber via which the inlet and outlet are in fluid communication, the closure forming a base of the chamber, such that when the fluid collection vessel is engaged with the cap the closure has a first orientation in which the at least one aperture is located within the periphery of the skirt in the base of the chamber and the fluid collection vessel is in communication with the chamber via the at least one aperture, and when the fluid collection vessel is removed from the cap the closure is rotated to a second orientation in which the at least one aperture is located externally of the periphery of the skirt and the base of the chamber; and
 conduits connected to the inlet and outlet.

2. A water trap suitable for use in a mechanical ventilation circuit, the water trap comprising a cap having formed therein an inlet and an outlet, a fluid collection vessel engageable with the cap, and a rotatable closure interposed between the cap and the fluid collection vessel and including at least one aperture, the fluid collection vessel is operably linked to the closure such that engagement or disengagement of the fluid collection vessel from the cap causes the closure to be rotated,
 wherein the cap is formed with an internal partition in the form of a skirt that extends into abutment with the closure to define a chamber via which the inlet and outlet are in fluid communication, the closure forming a base of the chamber, such that when the fluid collection vessel is engaged with the cap the closure has a first orientation in which the at least one aperture is located within the periphery of the skirt in the base of the chamber and the fluid collection vessel is in communication with the chamber via the at least one aperture, and when the fluid collection vessel is removed from the cap the closure is rotated to a second orientation in which the at least one aperture is located externally of the periphery of the skirt and the base of the chamber.

3. A water trap as claimed in claim 2, wherein the skirt depends from the underside of the cap and surrounds the openings of the inlet and outlet.

4. A water trap as claimed in claim 3, wherein the skirt is of elongate shape.

5. A water trap as claimed in claim 4, wherein the skirt is oblong in shape, having a length that is greater than its width.

6. A water trap as claimed in claim 2, wherein the skirt is formed separately from the cap.

7. A water trap as claimed in claim 6, wherein the cap includes formations which engage the skirt.

8. A water trap as claimed in claim 7, wherein said formations take the form of a rib onto which the skirt is pressed with an interference fit.

9. A water trap as claimed in claim 2, wherein a resilient seal is provided between the lower edge of the partition and surface of the closure.

10. A water trap as claimed in claim 9, wherein the seal is formed in elastomeric material and at least one of the remainder of the cap and skirt is formed in rigid plastics material.

11. A water trap as claimed in claim 10, wherein the component that carries the seal is formed using a two-shot injection molding process.

12. A water trap as claimed in claim 9, wherein the seal is affixed to the lower edge of the partition.

13. A water trap as claimed in claim 2, wherein the rotatable closure has the form of a disc.

14. A water trap as claimed in claim 13, wherein the rotatable disc is received within the cap with a snap fit.

15. A water trap as claimed in claim 2, wherein the collection vessel has a quick release type connection to the rest of the trap.

16. A water trap as claimed in claim 15, wherein the quick release type connection is a bayonet-type fitting.

17. A water trap as claimed in claim 2, wherein the skirt is integrally formed within the cap.

18. A method for making a water trap for use in a mechanical ventilation circuit, the method comprising:
   providing a cap having an inlet and an outlet;
   providing a fluid collection vessel for engagement or disengagement with the cap;
   interposing a rotatable closure with at least one aperture between the cap and the fluid collection vessel, wherein the fluid collection vessel is operably linked to the closure such that the engagement or disengagement of the fluid collection vessel from the cap causes the closure to be rotated,
   wherein the cap is formed with an internal partition in the form of a skirt that extends into abutment with the closure to define a chamber via which the inlet and outlet are in fluid communication, the closure forming a base of the chamber, such that with the engagement of the fluid collection vessel with the cap the closure has a first orientation in which the at least one aperture is located within the periphery of the skirt in the base of the chamber and the fluid collection vessel is in communication with the chamber via the at least one aperture, and with the disengagement of the fluid collection vessel with the cap the closure is rotated to a second orientation in which the at least one aperture is located externally of the periphery of the skirt and the base of the chamber.

19. The method as claimed in claim 18, wherein the skirt depends from the underside of the cap and surrounds the openings of the inlet and outlet.

20. The method as claimed in claim 19, wherein the skirt is of elongate shape.

21. The method as claimed in claim 20, wherein the skirt is oblong in shape, having a length that is greater than its width.

22. The method as claimed in claim 18 wherein the skirt is formed separately from the cap.

23. The method as claimed in claim 22, wherein the cap includes formations which engage the skirt.

24. The method as claimed in claim 23, wherein the formations take the form of a rib onto which the skirt is pressed with an interference fit.

25. The method as claimed in claim 18 further comprising providing a resilient seal between the lower edge of the partition and surface of the closure.

26. The method as claimed in claim 25, wherein the seal is formed in elastomeric material and at least one of the remainder of the cap and skirt is formed in rigid plastics material.

27. The method as claimed in claim 26, wherein the component that carries the seal is formed using a two-shot injection molding process.

28. The method as claimed in claim 25, wherein the seal is affixed to the lower edge of the partition.

29. The method as claimed in claim 18, wherein the rotatable closure has the form of a disc.

30. The method as claimed in claim 29, wherein the rotatable disc is received within the cap with a snap fit.

31. The method as claimed in claim 18, wherein the collection vessel has a quick release type connection to the rest of the trap.

32. The method as claimed in claim 31, wherein the quick release type connection is a bayonet-type fitting.

33. The method as claimed in claim 18 wherein the skirt is integrally formed within the cap.

* * * * *